US00PP24943P2

(12) United States Plant Patent
Leue

(10) Patent No.: US PP24,943 P2
(45) Date of Patent: Sep. 30, 2014

(54) ***HEUCHERA* PLANT NAMED 'CARNIVAL COFFEE BEAN'**

(50) Latin Name: *Heuchera×hybrida*
Varietal Denomination: Carnival Coffee Bean

(75) Inventor: Ellen Leue, Dekalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 286 days.

(21) Appl. No.: 13/507,886

(22) Filed: Aug. 3, 2012

(51) Int. Cl.
*A01H 5/00* (2006.01)

(52) U.S. Cl.
USPC ..... Plt./440

(58) Field of Classification Search
CPC ..... A01H 5/02; A01H 5/12; A01H 5/00
USPC ..... Plt./440
See application file for complete search history.

*Primary Examiner* — June Hwu
(74) *Attorney, Agent, or Firm* — Audrey Charles

(57) ABSTRACT

A new and distinct cultivar of *Heuchera* plant named 'Carnival Coffee Bean', characterized by its medium olive-green and brown colored foliage, rose-colored flowers, and moderately vigorous, mounded growth habit, is disclosed.

1 Drawing Sheet

Latin name of genus and species of plant claimed: *Heuchera×hybrida.*

Variety denomination: 'Carnival Coffee Bean'.

BACKGROUND OF THE INVENTION

The present invention relates to a new and distinct cultivar of *Heuchera* plant botanically known as *Heuchera×hybrida* and hereinafter referred to by the cultivar name 'Carnival Coffee Bean'.

The new cultivar originated in a controlled breeding program in Elburn, Ill. during May 2008. The objective of the breeding program was the development of *Heuchera* cultivars with unique foliage coloration and mounded growth habit.

The new *Heuchera* cultivar is the result of cross-pollination. The female (seed) parent of the new cultivar is the proprietary *Heuchera×hybrida* breeding selection coded 195-5, not patented, characterized by its light golden-brown colored foliage with a slight silver overlay, white-colored flowers, low vigor, and mounded growth habit. The male (pollen) parent of the new cultivar is the proprietary *Heuchera×hybrida* breeding selection coded 195-2, not patented, characterized by its light brownish-purple colored foliage, and moderately vigorous, mounded growth habit. The new cultivar was discovered and selected as a single flowering plant within the progeny of the above stated cross-pollination during March 2009 in a controlled environment in Elburn, Ill.

Asexual reproduction of the new cultivar by in vitro propagation since March 2009 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Carnival Coffee Bean' as a new and distinct cultivar of *Heuchera* plant:

1. Medium olive-green and brown colored foliage;
2. Rose-colored flowers; and
3. Moderately vigorous, mounded growth habit.

Plants of the new cultivar differ from plants of the female parent primarily in having a different foliage color, a different flower color, and increased growth vigor. Plants of the new cultivar differ from plants of the male parent primarily in having a different foliage color.

Of the many commercially available *Heuchera* cultivars, the most similar in comparison to the new cultivar is 'Chocolate Ruffles', U.S. Plant Pat. No. 8,965. However, in comparison, plants of the new cultivar differ from plants of 'Chocolate Ruffles' in at least the following characteristics:

1. Plants of the new cultivar have a foliage color that is more olive than plants of 'Chocolate Ruffles';
2. Plants of the new cultivar have a foliage margin that is less ruffled than plants of 'Chocolate Ruffles'; and
3. Plants of the new cultivar have a flower color different from plants of 'Chocolate Ruffles'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Carnival Coffee Bean'. The plants were grown in one-gallon containers for approximately one year in a greenhouse in West Chicago, Ill.

DETAILED BOTANICAL DESCRIPTION

Figure 1:
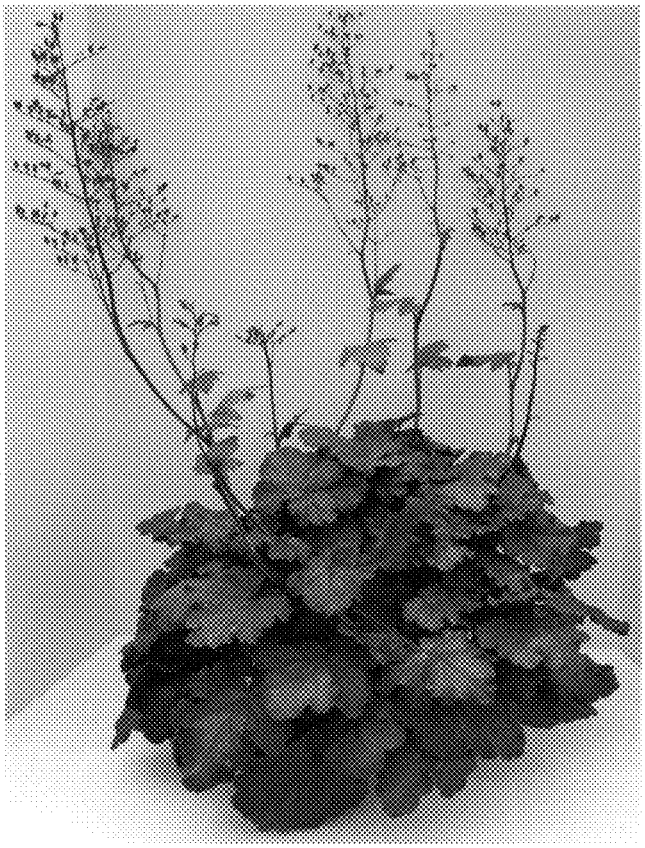
FIG. 1 illustrates a side view of the overall growth habit of 'Carnival Coffee Bean'.
Figure 2:
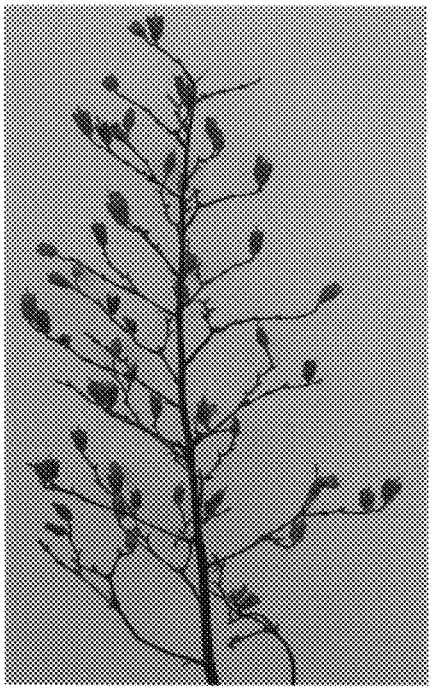
FIG. 2 illustrates a close-up view of an individual senescing inflorescence of 'Carnival Coffee Bean'.
Figure 3:
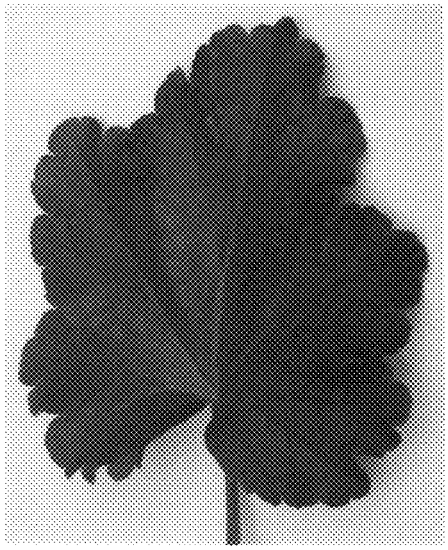
FIG. 3 illustrates a close-up view of an individual leaf of 'Carnival Coffee Bean'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in May 2012 under natural light conditions in West Chicago, Ill.

The following descriptions and measurements describe plants produced from in vitro plantlets and grown in a glass-covered greenhouse under conditions comparable to those used in commercial practice. The plants were grown in West Chicago, Ill. in one-gallon containers for approximately one year utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Heuchera×hybrida* cultivar Carnival Coffee Bean.

Parentage:

*Female parent*.—Proprietary *Heuchera×hybrida* breeding selection coded 195-5, not patented.

*Male parent*.—Proprietary *Heuchera×hybrida* breeding selection coded 195-2, not patented.

Propagation:

*Type*.—In vitro propagation is preferred, divisions are possible.

*Time to initiate roots in vitro*.—Approximately 10 days at 20° C.

*Time to initiate roots in greenhouse*.—Approximately 20 days at 20° C.

*Time to produce a rooted plantlet in summer*.—Approximately 42 days.

*Root description*.—Fine, fibrous; white to ivory in color.

*Rooting habit*.—Freely branching.

Plant description:

*Commercial crop time*.—Approximately 20 weeks from a rooted tissue culture plantlet to finish in a 1 gallon container.

*Growth habit and general appearance*.—Clump-forming herbaceous perennial, mounded foliage.

*Growth rate*.—Moderately vigorous.

*Outdoor plant performance*.—Use as bedding plants or in mixed-container plantings; at least tolerant to temperatures up to 35° C. and hardy to USDA zone 3.

*Size*.—Height from soil level to top of plant plane: Approximately 71.0 cm. Height from soil level to top of foliage: Approximately 26.0 cm. Width: Approximately 58.0 cm.

*Branching habit*.—No branching, basal rosettes of leaves on petioles. Number of rosettes per plant: Approximately 7.

Foliage description:

*General description*.—Moderately durable to environmental stresses. Quantity of leaves per rosette: Approximately 11. Fragrance: None. Form: Simple. Arrangement: Alternate.

*Leaves*.—Aspect: Blade is nearly perpendicular to petiole. Shape: Orbicular. Margin: Crenate, shallowly lobed. Apex: Broadly acute. Base: Cordate, sometimes moderately overlapping. Venation pattern: Palmate. Length of mature leaf: Approximately 12.5 cm. Width of mature leaf: Approximately 12.5 cm. Texture of upper surface: Dull, slightly rough, sparsely pubescent with short hairs. Texture of lower surface: Slightly glossy, moderately pubescent with short hairs. Color of upper surface of young foliage: Closest to 147B with a heavy overlay of 166B and venation of 166B to 166A. Color of lower surface of young and mature foliage: N186D. Color of upper surface of mature foliage: Closest to 147B with a slight overlay of 166B and venation of 147A or 166B in overlay regions.

*Petiole*.—Length: Approximately 14.0 cm. Diameter: Approximately 3.0 mm. Texture: Densely pubescent. Color: 147B with an overlay of 187B.

*Stipules*.—Two leafy stipules located at the base of each petiole. Apex: Narrow acute. Length: Approximately 1.8 cm. Width: Approximately 3.0 mm. Color: 147D with a faint overlay of 187D.

Flowering description:

*Flowering habit*.—'Carnival Coffee Bean' flowers once a year during late spring to midsummer under outdoor conditions.

*Lastingness of individual flower on the plant*.—Approximately 7 days.

Inflorescence description:

*General description*.—Type: Compound spike emerging from the base of the rosette with two to three cauline leaves. Fragrance: None. Length or height excluding the peduncle: Approximately 32.0 cm. Width: Approximately 14.0 cm. Quantity of inflorescences per plant: Approximately 5. Quantity of flowers per inflorescence: Approximately 90.

*Peduncle*.—Strength: Moderate. Aspect: Erect to approximately 30° angle from vertical. Length: Approximately 36.0 cm. Diameter at midpoint: Approximately 3.0 to 4.0 mm. Texture: Densely pubescent. Color: 147B with a heavy overlay of 187A.

Flower description:

*General description*.—Type: Single, campanulate, self-cleaning. Aspect: Drooping to slightly outward.

*Bud*.—Rate of opening: Generally takes 4 days for bud to progress from first color to fully open flower.

*Bud just before opening*.—Shape: Broadly obovate. Length: Approximately 4.0 mm. Diameter: Approximately 3.0 mm. Texture: Densely pubescent with a mixture of glandular and nonglandular hairs. Gland Color: N186A. Color: 54A.

*Corolla*.—Shape: Campanulate. Diameter: Approximately 5.0 mm. Depth: Approximately 7.0 mm.

*Petals*.—Quantity: 5. Arrangement: Single whorl. Shape: Narrowly elliptic. Appearance: Dull. Margin: Entire. Apex: Acute. Base: Lower half fused into hypanthium. Length: Approximately 7.0 mm. Width: Approximately 1.0 mm. Texture of upper and lower surfaces: Glabrous. Color of upper and lower surfaces when first and fully open: 56A.

*Calyx*.—Shape: Campanulate. Diameter: Approximately 5.0 mm. Depth: Approximately 7.0 mm.

*Sepals*.—Quantity per flower: 5. Shape: Elliptic. Appearance: Dull. Margin of free portion: Entire. Apex: Broadly acute. Base: Lower half fused into hypanthium. Length: Approximately 7.0 mm. Width at rim of hypanthium: Approximately 3.0 mm. Texture of upper surface: Glabrous. Texture of lower surface: Densely pubescent with a mixture of glandular and nonglandular hairs. Gland Color: N186A. Color of upper surface: 56A with 54B at tip. Color of lower surface: 54B, transitions to 53B with age.

*Pedicel*.—Strength: Moderate. Aspect: The pedicel of the central flower of each spikelet is directly on top of the secondary pedicel, pedicels of secondary and tertiary flowers of each spikelet have an average 40° angle from vertical. Length: Approximately 3.0 mm. Diameter: Less than 1.0 mm. Texture: Densely pubescent with a mixture of glandular and nonglandular hairs. Gland color: 187A. Color: 187A.

*Reproductive organs*.—Androecium: Quantity: 5 per flower. Anther shape: Ovate. Anther length: Less than 1.0 mm. Anther color: N25A. Filament length: Approximately 3.0 mm. Filament color: 56A. Pollen amount: Moderate. Pollen color: 25C. Gynoecium: Pistil quantity: 2 per flower. Pistil length: Approximately 8.0 mm. Stigma shape: Pointed. Stigma color: NN155C. Style length: Approximately 6.0 mm. Style color: NN155C, opaque. Ovary color: NN155C with 160A at base.

Seed and fruit production: Neither seed nor fruit production has been observed.

Disease and pest resistance: Resistance to pathogens and pests common to *Heuchera* has not been observed.

What is claimed is:

1. A new and distinct cultivar of *Heuchera* plant named 'Carnival Coffee Bean', substantially as herein shown and described.

* * * * *